US011382342B2

(12) United States Patent
Ito et al.

(10) Patent No.: US 11,382,342 B2
(45) Date of Patent: Jul. 12, 2022

(54) SILICA FORMULATION INCLUDING CASHEW NUT SHELL LIQUID OR THE LIKE

(71) Applicant: IDEMITSU KOSAN CO., LTD., Chiyoda-ku (JP)

(72) Inventors: Shinji Ito, Sodegaura (JP); Seika Ooiwa, Sodegaura (JP); Kyo Nagashima, Sodegaura (JP); Masami Mochizuki

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 231 days.

(21) Appl. No.: 14/775,174

(22) PCT Filed: Mar. 11, 2014

(86) PCT No.: PCT/JP2014/056310

§ 371 (c)(1),
(2) Date: Sep. 11, 2015

(87) PCT Pub. No.: WO2014/142113

PCT Pub. Date: Sep. 18, 2014

(65) Prior Publication Data

US 2016/0029670 A1 Feb. 4, 2016

(30) Foreign Application Priority Data

Mar. 13, 2013 (JP) ............................ JP2013-050946
Oct. 30, 2013 (JP) ............................ JP2013-225475

(51) Int. Cl.
*A23K 20/111* (2016.01)
*A23K 20/28* (2016.01)

(52) U.S. Cl.
CPC ............ *A23K 20/28* (2016.05); *A23K 20/111* (2016.05)

(58) Field of Classification Search
CPC .................................................... A23K 1/1756
See application file for complete search history.

(56) References Cited

U.S. PATENT DOCUMENTS

| | | | |
|---|---|---|---|
| 5,558,889 | A | 9/1996 | Rossi |
| 2007/0254070 | A1 | 11/2007 | Eepouse Alric et al. |
| 2009/0081292 | A1 | 3/2009 | Otomo et al. |
| 2012/0128817 | A1 | 5/2012 | Mochizuki et al. |

FOREIGN PATENT DOCUMENTS

| | | | |
|---|---|---|---|
| EP | 2 298 082 | A1 | 3/2011 |
| EP | 2 460 415 | A1 | 6/2012 |
| JP | 7-184561 | A | 7/1995 |
| JP | 2007-209224 | A | 8/2007 |
| WO | 2006/137289 | A1 | 12/2006 |
| WO | 2009/151048 | A1 | 12/2009 |
| WO | 2011/013592 | A1 | 2/2011 |

OTHER PUBLICATIONS

European Office Action dated Jun. 4, 2018 in European Patent Application No. 14763685.6, 6 pages.
International Search Report dated Jun. 17, 2014 in PCT/JP2014/056310 filed Mar. 11, 2014.

*Primary Examiner* — Elizabeth Gwartney
(74) *Attorney, Agent, or Firm* — Oblon, McClelland, Maier & Neustadt, L.L.P.

(57) ABSTRACT

A silica formulation comprising cashew nut shell liquid, anacardic acid, cardol, or cardanol, and silica particles, wherein the silica particles have adsorbed therein the cashew nut shell liquid, the anacardic acid, the cardol, or the cardanol, and wherein the silica particles have an average particle diameter of 150 μm or more.

15 Claims, 2 Drawing Sheets

After Coating

Before Coating

Coating Layer

Sipernat 2200

Sipernat 22

SILICA FORMULATION INCLUDING CASHEW NUT SHELL LIQUID OR THE LIKE

TECHNICAL FIELD

The present invention relates to a silica formulation including silica particles having adsorbed therein cashew nut shell liquid (CNSL), anacardic acid, cardol, or cardanol. The present invention also relates to coated granules including silica particles having adsorbed therein cashew nut shell liquid, anacardic acid, cardol, or cardanol, each of the silica particles being subject to surface coating, and a method for producing the coated granules.

BACKGROUND ART

Cashew nut shell liquid is an oily liquid contained in a shell of a fruit of a cashew nut tree (*Anacardium occidentale* L.). The cashew nut shell liquid mainly contains, as its components, anacardic acid, cardanol, cardol, and methylcardol.

A method for preparing a cashew nut shell liquid includes a heating method and a solvent-extraction method, but in general, the cashew nut shell liquid is used after converting the anacardic acid into a cardanol by heat treatment at a production district of the cashew nut.

The cashew nut shell liquid has the effect of causing a rash and thus requires care in handling. The rash can be caused by any of the main components of the anacardic acid, the cardanol, and the cardol. Thus, there has been a need for the development of a method for safely handling the cashew nut shell liquid.

Patent Document 1 describes a feed additive for livestock, the additive including a volatile product from a spice such as capsicum and peppers contained in a carrier, wherein the carrier is coated to prevent volatilization. In Patent Document 1, sawdust is used as the carrier, and a protein and alum are used as coagulating agents.

Patent Document 2 describes a formulation produced by preparing a W/O emulsion and impregnating a porous oil-adsorbing material with the emulsion to retain the liquid oil. In Patent Document 2, a hardened oil and the liquid oil are homogeneously mixed in advance to prevent leakage of the liquid oil; however, the formulation has an insufficient effect when referenced to the amount added.

In Patent Document 3, an oil-adsorbing formulation is produced by adsorbing a functional oil to a carrier such as silica under reduced pressure. The method according to Patent Document 3 has a drawback in that the method is limited to use of fine silica particles having an average particle diameter of, for example, 5.0-10.0 μm to improve the oil-adsorption rate.

In Patent Document 4, the inventors have succeeded in producing a raw silica material which prevents rash and improves handleability, by adsorbing cashew nut shell liquid or the like to an inorganic carrier such as silica. However, the examples in Patent Document 4 use silica particles having an average particle diameter of 100 μm, and do not encompass a silica formulation produced by adsorbing cashew nut shell liquid to silica particles having an average particle diameter of 150 μm or more. In Patent Document 4, the silica particles having adsorbed therein cashew nut shell liquid are not coated.

Patent Document 5 provides a formulation with improved handleability and safety, the formulation being produced by adsorbing cashew nut shell liquid to a silica carrier and then granulating and coating the resultant. However, in the examples in Patent Document 5, silica particles having an average particle diameter of 100 μm are used, and the silica particles having adsorbed therein cashew nut shell liquid are granulated to form granules having a diameter of 3.0 mm. The examples in Patent Document 5 do not encompass a silica formulation produced by adsorbing cashew nut shell liquid to silica particles having an average particle diameter of 150 μm or more.

When the raw silica material and the silica formulation according to Patent Documents 4 and 5, respectively, are allowed to stand for a long period, cashew nut shell liquid or the like may deposit. As cashew nut shell liquid is viscous liquid and solidifies at around 20° C., the liquid is very difficult to handle. Accordingly, there has been a need for the development of a technique for improving the handleability. In addition, contact with moisture or the like may result in elution of the cashew nut shell liquid or the like, and thus there has been a need for a technique for preventing the elution.

As described above, although techniques for adsorbing cashew nut shell liquid to silica and for coating granulated particles are known, a silica formulation produced by adsorbing cashew nut shell liquid to silica particles having an average particle diameter of 150 μm or more is not known. A silica formulation which includes silica particles having adsorbed therein cashew nut shell liquid, each of the silica particles being coated with a coating agent such as hardened oil, without agglomerating or granulating the silica particles, and a method for producing the formulation are also not known.

PRIOR ART DOCUMENTS

Patent Documents

[Patent Document 1] JP H7-184561 A
[Patent Document 2] WO2006/137289
[Patent Document 3] JP 2007-209224 A
[Patent Document 4] WO2009/151048
[Patent Document 5] WO2011/013592

SUMMARY OF THE INVENTION

The present invention is directed to prevent deposition of cashew nut shell liquid, anacardic acid, cardol, or cardanol (hereinafter also referred to as cashew nut shell liquid or the like) from an oil-adsorbing carrier (i.e., silica) at a low temperature and sticking of the deposited cashew nut shell liquid or the like thereby improving flowability of the cashew nut shell liquid or the like; and to prevent elution of cashew nut shell liquid or the like out of an oil-adsorbing carrier, the elution resulting in decrease in handleability of the formulation In other words, the present invention is directed to prevent skin-contact due to deposition and elution of cashew nut shell liquid or the like in a formulation (improve safety) and to improve the handleability.

The present invention is also directed to simplify the formulation process.

As a result of assiduous research intended to overcome the disadvantages described above, the present inventors have found that adsorption of cashew nut shell liquid to silica having an average particle diameter of 150 μm or more allows reduction in deposition of the cashew nut shell liquid.

The present inventors also have found that problems of deposition, elution, rash, and the like can be solved by additionally coating the silica having an average particle diameter of 150 μm or more and having adsorbed therein cashew nut shell liquid (raw silica material).

The present inventors also have found that adsorption of cashew nut shell liquid to silica particles at a temperature of 30° C. or higher to form a formulation allows reduction in elution of the cashew nut shell liquid.

In this way, the present inventors have completed the present invention.

The present invention relates to:

(1) a silica formulation comprising cashew nut shell liquid, anacardic acid, cardol, or cardanol, and silica particles, wherein the silica particles have adsorbed therein the cashew nut shell liquid, the anacardic acid, the cardol, or the cardanol, and wherein the silica particles have an average particle diameter of 150 μm or more;

(2) the formulation according to (1), wherein the surface of each of the silica particles is coated with a coating agent;

(3) the formulation according to (2), wherein the coating agent is a fatty acid, a hardened oil, palm oil, or oil derived therefrom;

(4) the formulation according to (3), wherein the coating agent has a melting point of 50° C. or higher;

(5) the formulation according to any one of (2)-(4), wherein the mass ratio of the coating agent to the silica formulation including the coating agent is 0.1-30:100;

(6) the formulation according to any one of (1)-(5), wherein the silica has an oil adsorption capacity per 100 g of the silica of 200 g or more;

(7) the formulation according to any one of (1)-(6), wherein the formulation is used for a feed;

(8) a method for producing a formulation which includes cashew nut shell liquid, anacardic acid, cardol, or cardanol, and silica particles, the method comprising adsorbing cashew nut shell liquid, anacardic acid, cardol, or cardanol to silica particles having an average particle diameter of 150 μm or more, and mixing, with stirring, the silica particles having adsorbed therein the cashew nut shell liquid, the anacardic acid, the cardol or the cardanol with a coating agent under heating;

(9) a method for producing a formulation which includes cashew nut shell liquid, anacardic acid, cardol, or cardanol, and silica particles, the method comprising adsorbing cashew nut shell liquid, anacardic acid, cardol, or cardanol to silica particles at a temperature of 30° C. or higher;

(10) the method according to (9), wherein the silica particles have an average particle diameter of 150 μm or more; and

(11) the method according to (9) or (10), further comprising mixing, with stirring, the silica particles having adsorbed therein the cashew nut shell liquid, the anacardic acid, the cardol, or the cardanol with a coating agent under heating.

Effect of the Invention

Reduction in deposition, elution, sticking, and the like of cashew nut shell liquid has led to improvement in safety and handleability during production, distribution, and use of the formulation.

Use of a fatty acid, a hardened oil, palm oil, or oil derived therefrom as the coating agent allows a coating process without use of water and a solvent. As a result, a drying process is omitted, which allows simplification of the overall process and reduction of the costs.

In addition, the oil adsorption process and the coating process can be performed in the same reactor in a series of process, which can simplify the processes and thus reduce costs.

MODE FOR CARRYING OUT THE INVENTION

Figure 1:
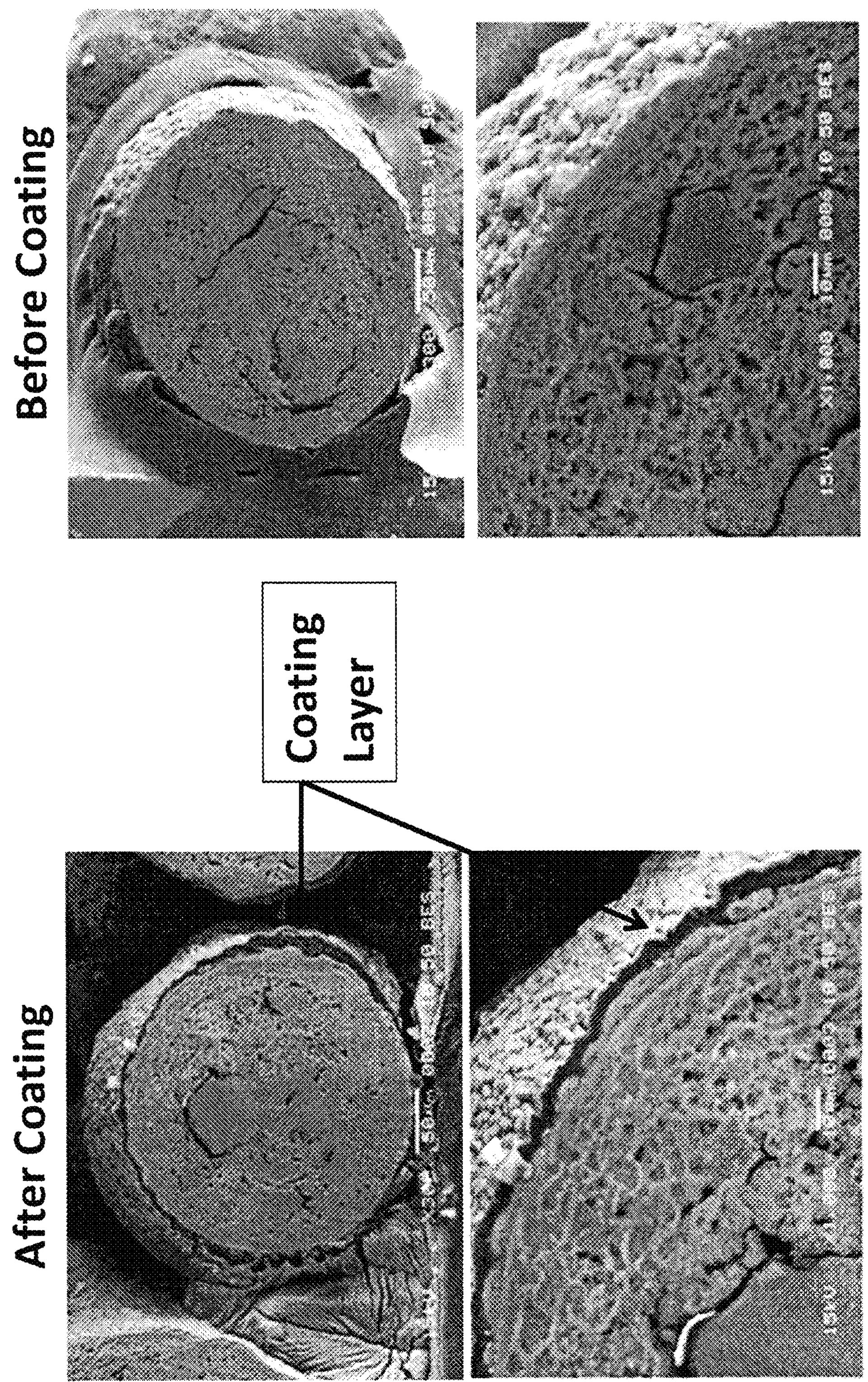
FIG. 1 shows cross-sectional views (photographs) of a formulation of the present invention before and after coating.

The silica formulation of the present invention includes cashew nut shell liquid, anacardic acid, cardol, or cardanol, and silica particles, the silica particles having adsorbed therein the cashew nut shell liquid, the anacardic acid, the cardol, or the cardanol and having an average particle diameter of 150 μm or more and preferably 250 μm or more. The upper limit of the average particle diameter is, for example, 500 μm, although the limit is not limited thereto. The average particle diameter of silica can be measured in accordance with the method of ISO 13320-1 or the like.

In the silica formulation of the present invention, the surface of each of the silica particles may be coated with a coating agent.

The silica formulation of the present invention may include a stabilizer and/or an antioxidant for cashew nut shell liquid.

It is noted that in the following description, silica particles having adsorbed therein cashew nut shell liquid or the like are sometimes referred to as raw silica material, that the formulation produced by coating the raw silica material with a coating agent is sometimes referred to as coated granules, and that the material and the granules are sometimes collectively referred to as a silica formulation.

Cashew nut shell liquid is an oily liquid contained in a shell of a fruit of a cashew nut tree (*Anacardium occidentale* L.). The cashew nut shell liquid contains, as its components, anacardic acid, cardanol, and cardol.

Usually, the anacardic acid is converted into cardanol by heat treatment.

Unheated cashew nut shell liquid extracted by compressing the shell of a cashew nut contains 55-80% by mass of anacardic acid, 5-20% by mass of cardanol, and 5-30% by mass of cardol, as described in J. Agric. Food Chem. 2001, 49, 2548-2551.

Heated cashew nut shell liquid obtained by heat treatment of unheated cashew nut shell liquid at a temperature of 70° C. or higher and preferably 130° C. or higher contains 0-10% by mass of anacardic acid, 55-80% by mass of cardanol, and 5-30% by mass of cardol, as the anacardic acid which is a main component of the unheated cashew nut shell liquid is converted into cardanol by decarboxylation.

Cashew nut shell liquid obtained by storing unheated cashew nut shell liquid at room temperature (20° C.) for about a year or more contains 0-10% by mass of anacardic acid, 55-80% by mass of cardanol, and 5-30% by mass of cardol, as the anacardic acid which is a main component of the unheated cashew nut shell liquid is converted into cardanol by decarboxylation.

Cashew nut shell liquid can be obtained as a vegetable oil extracted by compressing the shell of a cashew nut. The cashew nut shell liquid can also be obtained by extracting, for example, solvent-extracting a cashew nut shell. Further, the cashew nut shell liquid can be obtained by the process described in JP 8-231410 A such as, for example, solvent extraction.

The cashew nut shell liquid may be a commercially-available product.

The cashew nut shell liquid of the present invention may be heated cashew nut shell liquid obtained by heating unheated cashew nut shell liquid obtained as described above to 70° C. or higher and preferably 130° C. or higher. Alternatively, the cashew nut shell liquid may be obtained by storing unheated cashew nut shell liquid at room temperature (20° C.) for about a year or more.

The cashew nut shell liquid of the present invention may be obtained by extracting liquid (unheated cashew nut shell liquid) by compressing cashew nut shells and heating the liquid to 130° C.

The silica formulation of the present invention may contain anacardic acid, cardanol, or cardol, instead of cashew nut shell liquid.

The silica formulation of the present invention contains cashew nut shell liquid in an amount of 10-70% by mass, preferably 20-65% by mass, and more preferably 30-60% by mass, based on the total mass of the silica formulation. Inclusion of cashew nut shell liquid in an amount of 10% by mass or more can effectively provide, for example, an effect of improving rumen fermentation, an effect of preventing a bloat, an effect of treating a bloat, an effect of treating acidosis, an effect of controlling a disease caused by *Clostridium*, an effect of controlling a disease caused by *Coccidia*, an effect of increasing milk yields in a milk cow, an effect of controlling a perinatal disease in a milk cow, an effect of improving the reproductivity of a milk cow, and an effect of increasing body weight gain of livestock. It is preferred to include cashew nut shell liquid in an amount of 70% by mass or less, because hand rash can be prevented, and the handleability of the silica formulation can be maintained.

Examples of the anacardic acid used in the present invention include natural and synthetic anacardic acids and derivatives thereof. A commercial anacardic acid may also be used. The anacardic acid can be obtained by extracting cashew nut shell liquid from cashew nut shells with an organic solvent, as described in JP 8-231410 A, and eluting the anacardic acid with varying ratios of a solvent combination of n-hexane, ethyl acetate, and acetic acid, using, for example, silica gel column chromatography (see, for example, JP 3-240721 A and JP 3-240716 A). Such anacardic acid can be included in the silica formulation, a feed additive, and a feed in a similar amount to the cashew nut shell liquid.

Examples of the cardanol used in the present invention include natural and synthetic cardanols and derivatives thereof. The cardanol used in the present invention can be obtained by decarboxylating anacardic acid which is a main component of cashew nut shell liquid. Such cardanol can be included in the silica formulation, a feed additive, and a feed in a similar amount to the cashew nut shell liquid.

When heated cashew nut shell liquid is used, the heated cashew nut shell liquid preferably contains anacardic acid and cardanol in a mass ratio of 0:100-20:80.

Examples of the cardol used in the present invention include natural and synthetic cardols and derivatives thereof. The cardol used in the present invention can also be obtained by purification of cashew nut shell liquid.

The silica formulation of the present invention contains an oil adsorbent, and the cashew nut shell liquid, the anacardic acid, the cardanol, or the cardol (hereinafter sometimes referred to as cashew nut shell liquid or the like) is adsorbed to and contained in the oil adsorbent. An oil adsorbent for the silica formulation of the present invention is silica which has an average particle diameter of 150 μm or more. Preferably, an oil adsorbent for the present invention adsorbs 200 g or more of oil per 100 g of the adsorbent. The oil adsorption capacity (also referred to as adsorption capacity for oil or amount of oil adsorption) of silica can be measured in accordance with the method of ISO 787/5 or the like.

The silica formulation of the present invention may contain a stabilizer and/or an antioxidant for cashew nut shell liquid or the like. The stabilizer for cashew nut shell liquid or the like used in the present invention refers to a chelating agent which is a multidentate ligand forming coordinate bonds with a metal ion in cashew nut shell liquid or the like to produce a chelate compound.

Examples of the chelating agent used in the present invention include organic acid chelating agents, organic acid salt chelating agents, phosphoric acid chelating agents, phosphate chelating agents, amino polycarboxylic acid chelating agents, amino polycarboxylate chelating agents, neutral amino acid chelating agents, aluminosilicate chelating agents, phosphonic acid chelating agents, phosphonate chelating agents, and polymer chelating agents.

Examples of the organic acid chelating agents and the organic acid salt chelating agents include citric acid and salts thereof, malic acid and salts thereof, tartaric acid and salts thereof, succinic acid and salts thereof, gluconic acid and salts thereof, oxalic acid and salts thereof, glycolic acid and salts thereof, and propionic acid and salts thereof.

Examples of the phosphoric acid chelating agents and the phosphate chelating agents include orthophosphoric acid and salts thereof, pyrophosphoric acid and salts thereof, tripolyphosphoric acid and salts thereof, tetrapolyphosphoric acid and salts thereof, hexametaphosphoric acid and salts thereof, and phytic acid and salts thereof. Examples of the salts of orthophosphoric acid include sodium dihydrogen phosphate, potassium dihydrogen phosphate, ammonium dihydrogen phosphate, disodium hydrogen phosphate, dipotassium hydrogen phosphate, and diammonium hydrogen phosphate. Examples of the amino polycarboxylic acid chelating agents and the amino polycarboxylate chelating agents include ethylenediamine tetraacetic acid (EDTA) and salts thereof, ethylenediamine diacetic acid and salts thereof, hydroxyethyl ethylenediamine tetraacetic acid and salts thereof, diethylenetriamine pentaacetic acid and salts thereof, nitrilotriacetic acid and salts thereof, triethylenetetraamine hexaacetic acid and salts thereof, dicarboxymethyl glutamine hexaacetic acid and salts thereof, dicarboxymethyl glutamic acid tetrasodium salt, dihydroxymethyl glycine, 1,3-propanediaminetetraacetic acid and salts thereof, 1,3-diamino-2-hydroxypropane tetraacetic acid and salts thereof, phosphonobutane tricarboxylic acid and salts thereof, glutamic acid and salts thereof, cyclohexanediamine tetraacetic acid and salts thereof, iminodiacetic acid and salts thereof, N-(2-hydroxyethyl)iminodiacetic acid and salts thereof, N-(2-hydroxyethyl)ethylenediamine triacetic acid and salts thereof, glycol ether diaminetetraacetic acid and salts thereof, glutamic acid diacetic acid and salts thereof, aspartic acid diacetic acid and salts thereof, and dihydroxymethyl glycine.

Examples of the neutral amino acid chelating agents include glycine, alanine, leucine, cysteine, methionine, asparagine, and glutamine.

An example of the aluminosilicate chelating agents includes zeolite.

Examples of the phosphonic acid chelating agents and the phosphonate chelating agents include hydroxyethylidene diphosphonic acid and salts thereof, nitrilotris methylene phosphonic acid and salts thereof, and nitrilotris and salts thereof.

Examples of the polymer chelating agents include polyacrylic acid, polymaleic acid, and a copolymer of maleic acid and acrylic acid. Two or more of the chelating agents may be used in combination.

Examples of the antioxidant for cashew nut shell liquid or the like used in the present invention include ethoxyquin, t-butylhydroxytoluene, t-butylhydroxyanisole, t-butylhydroquinone, ascorbic acid and esters thereof, vitamin E, gallic acid and esters thereof, erythorbic acid, chlorogenic acid, sulfites, thiosulfates, phosphites, hypophosphites, and phosphates. Two or more of the antioxidants may be used in combination.

Although the silica formulation of the present invention can be obtained by adsorbing cashew nut shell liquid or the like on silica having an average particle diameter of 150 μm or more (oil-adsorption process), the silica formulation of the present invention is preferably coated granules obtained by adsorbing cashew nut shell liquid or the like to silica having an average particle diameter of 150 μm or more to form a raw silica material and then coating the surface of each of the raw silica material with a coating agent (coating process).

The coated granules of the present invention can be obtained, for example, in the following manner.

Silica particles having an average particle diameter of 150 μm or more (and another oil adsorbent where necessary) and cashew nut shell liquid or the like (with a stabilizer and/or an antioxidant added, where necessary) are mixed. Then, the silica particles having adsorbed therein the cashew nut shell liquid or the like (raw silica material) is coated with a coating agent under heating, where necessary.

In the present invention, after the oil-adsorption process, the raw silica material can be coated with a coating agent without granulating and shaping, where necessary, to provide the coated granules of the present invention.

Examples of the coating agent used in the present invention include oils such as hardened oils, palm oil, fatty acids, paraffins, and waxes. Two or more of these coating agents may be used in combination, or a mixture of them may be used.

Examples of the hardened oils used in the present invention include vegetable hardened oils such as hardened soybean oil, hardened palm oil, and hardened canola oil, although any oils can be used as long as they can release cashew nut shell liquid, anacardic acid, cardol, or cardanol.

Examples of the fatty acids used in the present invention include, for example, saturated fatty acids having a melting point higher than 50° C., more particularly, $C_{14}$ or greater saturated fatty acids such as myristic acid, palmitic acid, and stearic acid, and esters thereof, although any fatty acids can be used as long as they can release cashew nut shell liquid, anacardic acid, cardol, or cardanol.

The coating agent used in the present invention preferably has a melting point of 50° C. or higher. The coating agent used in the present invention is contained in an amount of 0.01-50% by mass, preferably 0.05-40% by mass, and more preferably 0.1-30% by mass, based on the total mass of the coated granules.

The coated granules in the present invention preferably have a mass ratio of the silica particles to the coating agent of 80-99.9:20-0.1.

Examples of the apparatus used in the oil adsorption process and the coating process in the present invention include, for example, mixers such as paddle mixers, ribbon mixers, rocking mixers, and cone mixers, although they are not limited thereto. In the present invention, the oil adsorption process and the coating process may be continuously performed in the same reactor or may be separately performed. In other words, it is only necessary that silica and cashew nut shell liquid are mixed to adsorb the cashew nut shell liquid to silica and after the adsorption, a coating agent is admixed, under heating, to the silica having adsorbed therein the cashew nut shell liquid to coat the surface of the silica.

In the production method of the present invention, use of oil melted under heating as the coating agent can omit the need to use a solvent and a drying process.

The production method of the present invention may be performed under ambient atmosphere or under reduced pressure.

In the production method of the present invention, although the oil-adsorption process may be performed at room temperature, it is recommended that the process is performed preferably at a heating temperature of 20-100° C., more preferably 30-80° C., and especially preferably 40-80° C. to make the oil-adsorption more efficient.

In the present invention, it is found that adsorption of cashew nut shell liquid, anacardic acid, cardol, or cardanol to silica particles at a temperature of 30° C. or higher to form a formulation allows reduction in elution of the active ingredients of the cashew nut shell liquid or the like. Such effect is not restricted to the case in which silica having an average particle diameter of 150 μm or more is used.

Accordingly, the present invention also relates to a method for producing a formulation which includes cashew nut shell liquid, anacardic acid, cardol, or cardanol, and silica particles, the method including a step of adsorbing cashew nut shell liquid, anacardic acid, cardol, or cardanol to silica particles at a temperature of 30° C. or higher (preferably 30-80° C., and more preferably 40-80° C.).

Preferably, the coating process is performed at a heating temperature adjusted depending on the melting point of the coating agent to be used. Although it is only necessary that the heating temperature during the addition of the coating agent is higher than the melting point, the heating temperature preferably is higher than the melting point of the coating agent to be used by 5-50° C.

When the coating agent is used to coat the silica particles, the apparatus as described above can be used. In particular, the coating process is performed as described below:

Cashew nut shell liquid or the like is adsorbed to silica particles having an average particle diameter of 150 μm or more.

An appropriate amount of a coating agent is admixed with the silica particles having adsorbed therein the cashew nut shell liquid or the like (raw silica material) with stirring at an appropriate temperature.

After the admixing with stirring, the coated silica particles are cooled, where necessary.

The silica formulation of the present invention is suitably used as an agent for improving rumen fermentation for a ruminant, an agent for preventing a bloat, an agent for treating a bloat, an agent for treating abomasal displacement, an agent for treating acidosis, an agent for controlling a disease caused by *Clostridium*, an agent for controlling a disease caused by *Coccidia*, an agent for increasing milk yields in a milk cow, an agent for controlling a perinatal disease in a milk cow, an agent for improving the reproductivity of a milk cow, and an agent for increasing body weight gain of livestock. The silica formulation of the present invention can be used as a feed additive.

Although the feed additive of the present invention is not specifically limited as long as the additive contains the silica formulation of the present invention, the additive may additionally contain an optional component such as a component effective at promoting growth of ruminants, a nutritional supplement component, and a component which improves the storage stability. Examples of such optional component include, for example, probiotics such as *Enterococcus* spp., *Bacillus* spp., and *Bifidobacterium* spp.; enzymes such as amylase and lipase; vitamins such as L-ascorbic acid, choline chloride, inositol, and folate; minerals such as potassium chloride, iron citrate, magnesium oxide, and phosphates; amino acids such as DL-alanine, DL-methionine, and L-lysine; organic acids such as fumaric acid, butyric acid, lactic acid, and acetic acid, and salts thereof; antioxidants such as ethoxyquin, dibutylhydroxytoluene, butylhydroxyanisol, ferulic acid, vitamin C, and vitamin E; fungicides such as calcium propionate; binders such as CMC, casein sodium, and sodium polyacrylate; emulsifiers such as lecithin, glycerin fatty acid ester and sorbitan fatty acid ester; pigments such as astaxanthin and canthaxanthin; and flavoring agents such as various esters, ethers, and ketones.

The feed additive of the present invention can be combined with another feed component used in conventional feeds to form a feed. The type of the feed and the components other than the silica formulation are not specifically limited.

When the feed of the present invention is fed to, for example, a ruminant such as cattle, a goat, and sheep, the amount of the feed to be fed can be appropriately adjusted depending on the kind, body weight, age, sex, and health condition of the animal, the feed components, and the like, provided that cashew nut shell liquid contained in the feed is preferably fed in an amount of 0.005-500 g per animal per day, more preferably 0.05-100 g per animal per day, and still more preferably 0.5-50 g per animal per day.

Routine procedures can be used to feed and raise animals depending on the kind of the animals.

EXAMPLES

1. Extraction of Unheated Cashew Nut Shell Liquid 500 kg of cashew nut shells were obtained from Cashew Co., Ltd. and compressed to produce 158 kg of cashew nut shell liquid (unheated CNSL).

The composition of the CNSL was determined in the manner as described below. An HPLC system (Waters 600, Nihon Waters K.K.), a detector (Waters 490E, Nihon Waters K.K.), a printer (Chromatopac C-R6A, Shimadzu Corp.), and a column (Supelcosil LC18, Supelco, Inc.) were used. The analysis was carried out under the conditions of a solvent composition of acetonitrile: water: acetic acid=80:20:1 (based on volume), a flow rate of 2 ml/min, and an absorbance of 280 nm.

The unheated cashew nut shell liquid contained 61.8% by mass of anacardic acid, 8.2% by mass of cardanol, and 19.9% by mass of cardol.

2. Preparation of Silica Formulation (1) The following types of silica available from Evonik, Rhodia, and Oriental Silicas Corporation were used. The average particle diameters described in the catalogs are shown in Table 1.

TABLE 1

| Silica | Average Particle diameter (μm) | Amount of Oil Adsorption (ml/100 g) | Supplier |
|---|---|---|---|
| Sipernat 22 | 110 | 270 | Evonik |
| 255LD | 173 | 211 | Oriental Silicas Corporation |
| Tixosil 68 | 250 | 250 | Rhodia |
| Sipernat 2200 | 320 | 250 | Evonik |

(2) The following coating agents available from Wako Pure Chemical Industries, Ltd. and Yokozeki Oil & Fat Industries Co., Ltd. were used.

TABLE 2

| Coating Agent | Melting Point (° C.) | Supplier |
|---|---|---|
| Lauric Acid | 45 | Wako Pure Chemical Industries, Ltd. |
| Myristic Acid | 55 | Wako Pure Chemical Industries, Ltd. |
| Hardened Palm Oil | 59 | Yokozeki Oil & Fat Industries Co., Ltd. |
| Palmitic Acid | 64 | Wako Pure Chemical Industries, Ltd. |
| Hardened Soybean Oil | 68 | Yokozeki Oil & Fat Industries Co., Ltd. |
| Stearic Acid | 70 | Wako Pure Chemical Industries, Ltd. |

(3) Cashew Nut Shell Liquid

As described above, cashew nut shells were obtained from Cashew Co., Ltd. and compressed to produce cashew nut shell liquid.

(4) Oil-Adsorption Process

A 300 ml 3-neck separable flask equipped with an addition funnel and a paddle stirrer was prepared.

The flask was charged with 52 g of silica having a respective particle diameter shown in Table 1 and placed in a hot bath adjusted to heat the silica to a specified temperature. 68 g of cashew nut shell liquid in the addition funnel was added dropwise with stirring over a period of about 40 minutes. After completion of the addition, stirring was continued for 5 minutes thereby completing the oil-adsorption process (Production Example 1).

(5) Integrated Production (Coating Process)

To the raw silica material produced as described above in (4) Oil-Adsorption Process, 24 g of fractured hardened palm oil (from Yokozeki Oil & Fat Industries Co., Ltd.) was added and homogeneously mixed with stirring. The resultant mixture was stirred for 10 minutes in a hot bath at 70° C. and cooled while stirring similarly, thereby completing the coating process (Production Example 2).

(6) Separate Production (Coating Process)

The silica containing the cashew nut shell liquid produced as described above in (4) Oil-Adsorption Process was used to produce coated granules using various coating agents. In the coating process using a small amount of a coating agent, a 500 ml eggplant flask was used, and the flask was rotated in a hot bath to perform the process.

In particular, a 500 ml eggplant flask was charged with 10 g of the silica containing the cashew nut shell liquid produced as described above in (4) Oil-Adsorption Process and 2 g of the fractured coating agent, and then rotated for homogeneous mixing. Then, the eggplant flask was placed in a hot bath adjusted to heat to the mixture to the melting point of the coating agent added, and rotated for about 10 minutes to coat the silica. This procedure was used to produce formulations coated with the 6 kinds of coating agents shown in Table 2 (lauric acid, myristic acid, palmitic acid, stearic acid, hardened palm oil, and hardened soybean oil) (Production Examples 3-8).

3. Performance Evaluation (1) Electron Microscopical Analysis

FIG. 1 shows an electron micrograph of a formulation produced. As can be seen, the coating process using a coating agent allowed formation of a coating layer.

(2) Determination of Deposition for Particle Diameter of Silica (Example 1)

Each of the silica formulations in Production Example 1 (oil-adsorption temperature: 40° C.) (Table 1) was allowed to stand at 4° C. for 4 days. Then, it was determined whether the cashew nut shell liquid was deposited on the surface of the silica (Table 3).

TABLE 3

| Silica | Average Particle diameter (μm) | Amount of Oil Adsorption (ml/100 g) | Supplier | Deposition |
|---|---|---|---|---|
| Sipernat 22 | 110 | 270 | Evonik | Yes |
| 255LD | 173 | 211 | Oriental Silicas Corporation | No |
| Tixosil 68 | 250 | 250 | Rhodia | No |
| Sipernat 2200 | 320 | 250 | Evonik | No |

Figures 2, 3:
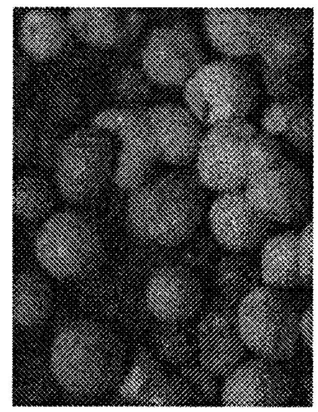
FIG. 2 shows the surface (photograph) of silica having an average particle diameter of 110 μm and having adsorbed therein cashew nut shell liquid.
FIG. 3 shows the surface (photograph) of silica having an average particle diameter of 320 μm and having adsorbed therein cashew nut shell liquid.

FIG. 2 shows that the cashew nut shell liquid was deposited on the surface of the silica having an average particle diameter of 110 μm. On the other hand, deposition was not observed on the surface of the silica having an average particle diameter of 170, 250, and 320 μm (FIG. 3).

(3) Evaluation of Elution of Cashew Nut Shell Liquid for Various Coated Granules (Example 2 (Oil-Adsorption Temperature: 40° C.))

1 g of the coated granules produced as described above in (4) and (6) in 2. Preparation of Silica Formulation (Sipernat 2200 silica was used) were added to 40 ml of water and allowed to stand at 20° C. for an hour. Then, the coated granules were collected. The cashew nut shell liquid remaining in the granules was extracted with ethyl acetate to collect the liquid, and the amount of the elution was determined. The results are shown in Table 4.

TABLE 4

| Coating Agent | Melting Point (° C.) | Supplier | Elution Rate (%) |
|---|---|---|---|
| None | — | — | 90 |
| Lauric Acid | 45 | Wako Pure Chemical Industries, Ltd. | 86 |
| Myristic Acid | 55 | Wako Pure Chemical Industries, Ltd. | 32 |
| Hardened Palm Oil | 59 | Yokozeki Oil & Fat Industries Co., Ltd. | 21 |
| Palmitic Acid | 64 | Wako Pure Chemical Industries, Ltd. | 7 |
| Hardened Soybean Oil | 68 | Yokozeki Oil & Fat Industries Co., Ltd. | 8 |
| Stearic Acid | 70 | Wako Pure Chemical Industries, Ltd. | 11 |

Table 4 shows that the materials having a higher melting point than myristic acid are highly effective in suppressing the elution. Thus, it is believed that the ability of a coating agent to suppress the elution is associated with the melting point of the coating agent.

(4) Evaluation of Elution of Cashew Nut Shell Liquid for Various Types of Silica (Example 3 (Oil-Adsorption Temperature: 25° C.))

Coated formulations were produced using hardened palm oil in the same manner as the manner described above in (4) and (5) in 2. Preparation of Silica Formulation. The elution was evaluated in the same manner as the manner described in (3) in 3. Performance Evaluation, except that the resultant coated formulations were allowed to stand for 15 minutes. The results are shown in Table 5.

TABLE 5

| Silica | Average Particle diameter (μm) | Amount of Oil Adsorption (ml/100 g) | Coating | Elution Rate (%) |
|---|---|---|---|---|
| Sipernat 22 | 110 | 270 | Yes | 20 |
| | | | No | 80 |
| 255LD | 173 | 211 | Yes | 19 |
| | | | No | 55 |
| Tixosil 68 | 250 | 250 | Yes | 11 |
| | | | No | 50 |
| Sipernat 2200 | 320 | 250 | Yes | 10 |
| | | | No | 44 |

Table 5 shows that any of the types of silica can provide a silica formulation having an effect of suppressing the elution.

(5) Evaluation of Elution of Cashew Nut Shell Liquid for Various Types of Silica with Different Oil-Adsorption Temperatures (Example 4)

The silica formulations in Production Example 1 were evaluated for the elution in the same manner as the manner described above in (3) in 3. Performance Evaluation, except that the resultant coated formulations were allowed to stand for 15 minutes. The results are shown in Table 6. Note that evaluation was performed at an oil-adsorption temperature of 20-80° C.

Evaluation of Elution of Cashew Nut Shell Liquid

—Elution Rate in Case in Which Cashew Nut Shell Liquid was Adsorbed to Various Silica at Different Adsorption Temperatures—

TABLE 6

| Silica | Average Particle diameter (μm) | Amount of Oil Adsorption (ml/100 g) | Oil Adsorption Temperature (° C.) | Elution Rate (%) |
|---|---|---|---|---|
| Sipernat22 | 110 | 270 | 20 | 86 |
| | | | 40 | 50 |
| | | | 60 | 30 |
| | | | 80 | 20 |
| 255LD | 173 | 211 | 20 | 78 |

TABLE 6-continued

| Silica | Average Particle diameter (μm) | Amount of Oil Adsorption (ml/100 g) | Oil Adsorption Temperature (° C.) | Elution Rate (%) |
|---|---|---|---|---|
| | | | 40 | 35 |
| | | | 60 | 20 |
| | | | 80 | 15 |
| Tixosil 68 | 250 | 250 | 20 | 74 |
| | | | 40 | 21 |
| | | | 60 | 16 |
| | | | 80 | 13 |
| Sipernat2200 | 320 | 250 | 20 | 62 |
| | | | 40 | 18 |
| | | | 60 | 12 |
| | | | 80 | 11 |

Table 6 shows that if cashew nut shell liquid is adsorbed at a temperature of 30° C. or higher, any of the types of silica can provide a formulation which can significantly suppress elution of the cashew nut shell liquid. In addition, it is found that use of silica having a larger particle diameter allows further suppression of the elution.

(6) Evaluation of Elution of Cashew Nut Shell Liquid for Various Coated Granules with Different Oil-Adsorption Temperatures (Example 5)

Coated formulations were produced using hardened palm oil in the same manner as the manner described above in (4) and (5) in 2. Preparation of Silica Formulation, except that cashew nut shell liquid was adsorbed at a temperature of 25° C. or 50° C.

The resultant coated formulations were evaluated for the elution in the same manner as the manner described above in (3) in 3. Performance Evaluation, except that the resultant coated formulations were allowed to stand for 15 minutes. The results are shown in Table 7.

Evaluation of Elution of Cashew Nut Shell Liquid —Elution Rate in Case in Which Cashew Nut Shell Liquid was Adsorbed to Silica at Different Adsorption-Temperatures and Silica was Coated with Coating Agent—

TABLE 7

| Silica | Average Particle diameter (μm) | Amount of Oil Adsorption (ml/100 g) | Oil Adsorption Temperature (° C.) | Coating | Elution Rate (%) |
|---|---|---|---|---|---|
| Sipernat 2200 | 320 | 250 | 25 | Yes | 10 |
| | | | | No | 44 |
| | | | 50 | Yes | 5 |
| | | | | No | 18 |

Table 7 shows that a higher oil-adsorption temperature and coating with a coating agent allow further suppression of the elution.

INDUSTRIAL APPLICABILITY

The present invention can provide a silica formulation which includes cashew nut shell liquid or the like, with improved safety and handleability. The present invention can also provide a simpler method for producing coated granules. The formulation and the production method of the present invention are useful in livestock field.

The invention claimed is:

1. A silica formulation, comprising:
cashew nut shell liquid;
silica particles in which the cashew nut shell liquid is adsorbed; and
a coating agent coating a surface of each of the silica particles and comprising a fatty acid, a hardened oil, palm oil, or oil derived therefrom,
wherein the silica particles have an average particle diameter of 150 μm to 320 μm,
the silica formulation comprises the cashew nut shell liquid in an amount of 20 to 60% by mass based on a total mass of the silica particles and the cashew nut shell liquid, and
when the silica formulation is stored at 4° C. for 4 days, the cashew nut shell liquid does not deposit on the surface of the silica formulation.

2. The silica formulation according to claim 1, wherein the coating agent comprises a fatty acid, a hardened oil, or palm oil.

3. The silica formulation according to claim 2, wherein the coating agent has a melting point of 50° C. or higher.

4. The silica formulation according to claim 1, wherein a mass ratio of the coating agent to the silica formulation including the coating agent is 0.1-30:100.

5. The silica formulation according to claim 1, wherein the silica particles have an oil-adsorption capacity per 100 g of the silica of 200 g or more.

6. A feed, comprising:
the silica formulation according to claim 1.

7. The silica formulation according to claim 1, wherein the silica formulation comprises the cashew nut shell liquid in an amount of 30 to 60% by mass, based on a total mass of the silica particles and the cashew nut shell liquid.

8. The silica formulation according to claim 1, wherein the coating agent comprises at least one selected from the group consisting of lauric acid, myristic acid, hardened palm oil, palmitic acid, hardened soybean oil, and stearic acid.

9. The silica formulation according to claim 1, wherein the coating agent has a melting point of 50° C. or higher and comprises a fatty acid, a hardened oil, or palm oil.

10. The silica formulation according to claim 1, wherein the silica formulation is produced by a process comprising adding the cashew nut shell liquid to the silica particles at a temperature of 40° C. to 80° C.

11. The silica formulation according to claim 1, wherein the coating agent comprises hardened palm oil.

12. A silica formulation, comprising:
cashew nut shell liquid; and
silica particles in which the cashew nut shell liquid is adsorbed,
wherein the silica formulation does not have a coating on the silica particles,
the silica particles have an average particle diameter of 150 μm or more, and
the silica formulation comprises cashew nut shell liquid in an amount of 20 to 70% by mass based on a total mass of the silica formulation.

13. The silica formulation according to claim 12,
wherein, when the silica formulation is stored at 4° C. for 4 days, the cashew nut shell liquid does not deposit on the surface of the silica particles, and
the silica particles have an average particle diameter of 150 μm to 320 μm.

14. A method for producing the silica formulation of claim 1, the method comprising:
adsorbing cashew nut shell liquid to silica particles having an average particle diameter of 150 μm to 320 μm; and mixing, with stirring, the silica particles in which the cashew nut shell liquid is adsorbed with a coating agent while heating, wherein an amount of the cashew nut shell liquid adsorbed in the silica particles is 20 to 60% by mass based on a total mass of the cashew nut shell liquid and the silica particles.

15. The method of claim 14, wherein the cashew nut shell liquid is adsorbed to the silica particles at a temperature of 30° C. or higher.

* * * * *